United States Patent [19]
Berg et al.

[11] Patent Number: 4,715,933
[45] Date of Patent: Dec. 29, 1987

[54] SEPARATION OF N-PROPANOL FROM 2-BUTANOL BY EXTRACTIVE DISTILLATION

[76] Inventors: Lloyd Berg; Mark G. Vosburgh, both of 1314 S. Third Ave., both of Bozeman, Mont. 59715

[21] Appl. No.: 776,450

[22] Filed: Sep. 16, 1985

[51] Int. Cl.$^4$ .................. B01D 3/40; C07C 29/84
[52] U.S. Cl. ...................... 203/51; 203/60; 203/61; 203/71; 568/913
[58] Field of Search .......... 203/60, 61, 51, 71; 568/918, 913

[56] References Cited

U.S. PATENT DOCUMENTS

| | | | |
|---|---|---|---|
| 2,551,584 | 5/1951 | Carlson et al. | 203/51 |
| 2,552,412 | 5/1951 | Drout et al. | 203/84 |
| 2,559,519 | 7/1951 | Smith et al. | 203/64 |
| 2,559,520 | 7/1951 | Smith et al. | 203/64 |
| 2,570,205 | 10/1951 | Carlson et al. | 203/58 |
| 2,575,243 | 11/1951 | Carlson et al. | 203/60 |
| 2,591,712 | 4/1952 | Morrell et al. | 203/84 |
| 2,591,713 | 4/1952 | Morrell et al. | 203/84 |
| 2,706,707 | 4/1955 | Morrell et al. | 203/57 |

*Primary Examiner*—Wilbur Bascomb

[57] ABSTRACT n-Propanol and 2-butanol cannot be separated from each other by distillation because of the proximity of their boiling points. n-Propanol can be readily separated from 2-butanol using extractive distillation in which the extractive agent is a higher boiling oxygenated organic compound or a mixture of two or more of these. Typical examples of effective agents are: methyl benzoate; benzoic acid and methyl benzoate; cinnamic acid, phthalic anhydride and methyl benzoate.

3 Claims, No Drawings

SEPARATION OF N-PROPANOL FROM 2-BUTANOL BY EXTRACTIVE DISTILLATION

FIELD OF THE INVENTION

This invention relates to a method for separating n-propanol from 2-butanol using certain higher boiling liquids as the extractive agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form a minimum azeotrope with them. Usually the extractive agent is introduced a few plates from the top of the column to insure that none of the extractive agent is carried over with the lowest boiling component. This usually requires that the extractive agent boil about twenty Centigrade degrees or more higher than the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

n-Propanol and 2-butanol are two of the most widely used alcohols in commerce today. When they are used as solvents, they frequently end up as a mixture of solvents. Whenever practical, it is mandatory to recover the solvent and re-use it. The usual way of recovering liquid components is by distillation in a multiplate rectification column. n-Propanol boils at 97.2° C., 2-butanol at 99.5° C. and these two have a relative volatility of 1.07, making it virtually impossible to separate these two by ordinary rectification.

Extractive distillation would be an attractive method of effecting the separation of n-propanol from 2-butanol if agents can be found that (1) will alter the relative volatility between n-propanol and 2-butanol, (2) form no azeotrope with n-propanol or 2-butanol and (3) are easy to recover from 2-butanol, that is boil sufficiently above 2-butanol to make the separation by rectification possible with only a few theoretical plates.

Extractive distillation typically requires the addition of an equal amount to twice as much extractive agent as the n-propanol-2-butanol on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required in azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. We recommend twenty Centigrade degrees or more difference. It is also desirable that the extractive agent be miscible with the 2-butanol otherwise it will form a two phase azeotrope with it and some other method of separation will have to be employed.

Smith, U.S. Pat. No. 2,559,520 described an extractive distillation process to separate n-propanol from 2-butanol using 1,3-butanediol as the agent and reported a relative volatility of 1.79. In our Table 1 below, we report a relative volatility of only 1.01 for this agent. Smith, U.S. Pat. No. 2,559,519 report a relative volatility of 2.21 using ethylene glycol butyl ether; we get 1.16 with this agent. He reports a relative volatility of 1.97 with diethylene glycol ethyl ether; we get 1.05 for this agent. Carlson & Smith, U.S. Pat. No. 2,570,205 report a relative volatility of 2.22 using sulfolane; we get 1.05 for this agent. These data are summarized in Table 1. We suspect that in 1948, they did not have accurate analytical methods for their liquid mixtures.

TABLE 1
Comparison With Results In The Literature.

| Compounds | Investigator | Relative Volatility |
|---|---|---|
| 1,3-Butanediol | Berg & Vosburgh | 1.01 |
| | Smith, 2,559,520 | 1.79 |
| Ethylene glycol butyl ether | Berg & Vosburgh | 1.16 |
| | Smith, 2,559,519 | 2.21 |
| Diethylene glycol ethyl ether | Berg & Vosburgh | 1.05 |
| | Smith, 2,559,519 | 1.97 |
| Sulfolane | Berg & Vosburgh | 1.05 |
| | Carlson & Smith, 2,570,205 | 2.22 |

OBJECTIVE OF THE INVENTION

The object of this invention is to provide a process or method of extractive distillation that will enhance the relative volatility of n-propanol from 2-butanol in their separation in a rectification column. It is a further objective of this invention to identify organic compounds which are stable, can be separated from 2-butanol by rectification with relatively few plates and can be recycled to the extractive distillation column and re-used with little decomposition.

SUMMARY OF THE INVENTION

The objects of this invention are provided by a process for separating n-propanol from 2-butanol which entails the use of certain oxygenated organic compounds as the agent in extractive distillation.

DETAILED DESCRIPTION OF THE INVENTION

We have discovered that certain oxygenated organic compounds, some individually but principally as mixtures, will effectively enhance the relative volatility between n-propanol and 2-butanol and permit the separation of pure n-propanol from 2-butanol by rectification when employed as the agent in extractive distillation. Table 2 lists benzoic acid, its mixtures and approximate proportions that we have found to be effective. Table 3 is a similar listing for cinnamic acid, Table 4 for salicylic acid, Table 5 for aromatic anhydrides and Table 6 for methyl benzoate and methyl salicylate. The data in Tables 2, 3, 4, 5 and 6 were obtained in in a vapor-liquid equilibrium still. In each case the starting material was the 50—50% n-propanol-2-butanol mixture. The ratios are the parts of extractive agent used per part of n-propanol-2-butanol mixture. The relative volatilities are listed for each of the two ratios employed. The compounds that are effective as extractive agents when used alone are methyl benzoate, methyl salicylate, hexahydro-phthalic anhydride and methyl hexahydro-phthalic anhydride. The compounds which are effective when used in mixtures of two or more components are benzoic acid, benzyl benzoate, phthalic anhydride, methyl tetrahydro-phthalic anhydride, salicylic acid, cinnamic acid, sulfolane, trimellitic anhydride and butyl benzyl phthalate. The ratios in Tables 2, 3, 4, 5 and 6 are the parts of extractive agent used per part of n-propanol-2-butanol mixture. The two relative volatilities correspond to the two different ratios. For example, in Table 6, one part of methyl benzoate with one part of n-propanol-2-butanol mixture gives a relative volatility of 1.20, 6/5 parts of methyl benzoate give 1.24. In Table 2 one half part of benzoic acid mixed with one half part of methyl benzoate with one part of n-propanol-2-butanol mixture gives a relative volatility of 1.23, 3/5 parts of benzoic acid plus 3/5 parts of methyl benzoate give 1.24.

TABLE 2

Extractive Agents Which Contain Benzoic Acid

| Compounds | Ratios | | Relative Volatilities | |
|---|---|---|---|---|
| None | — | | 1.07 | |
| Benzoic acid, Benzyl benzoate | $(1/2)^2$ | $(3/5)^2$ | 1.17 | 1.20 |
| Benzoic acid, Methyl benzoate | " | " | 1.23 | 1.24 |
| Benzoic acid, Methyl salicylate | " | " | 1.21 | 1.23 |
| Benzoic acid, Phthalic anhydride, Methyl benzoate | $(1/3)^3$ | $(2/5)^3$ | 1.19 | 1.20 |
| Benzoic acid, Phthalic anhydride, Methyl salicylate | " | " | 1.25 | 1.26 |
| Benzoic acid, Salicylic acid, Methyl THphthalic anh. | " | " | 1.19 | 1.19 |
| Benzoic acid, Salicylic acid, Methyl benzoate | " | " | 1.26 | 1.24 |
| Benzoic acid, Salicylic acid, Benzyl benzoate | " | " | 1.18 | 1.19 |
| Benzoic acid, Benzyl benzoate, Hexahydro phthalic anh | " | " | 1.16 | |

TABLE 3

Extractive Agents Which Contain Cinnamic Acid

| Compounds | Ratios | | Relative Volatilities | |
|---|---|---|---|---|
| Cinnamic acid, Methyl benzoate | $(1/2)^2$ | $(3/5)^2$ | 1.19 | 1.21 |
| Cinnamic acid, Methyl salicylate | " | " | 1.18 | 1.25 |
| Cinnamic acid, Sulfolane | " | " | 1.09 | 1.22 |
| Cinnamic acid, Phthalic anhydride, Methyl benzoate | $(1/3)^3$ | $(2/5)^3$ | 1.24 | 1.28 |
| Cinnamic acid, Methyl salicylate, Trimellitic anhyd. | " | " | 1.22 | 1.23 |

TABLE 4

Extractive Agents Which Contain Salicylic Acid

| Compounds | Ratios | | Relative Volatilities | |
|---|---|---|---|---|
| Salicylic acid, Benzyl benzoate | $(1/2)^2$ | $(3/5)^2$ | 1.20 | 1.20 |
| Salicylic acid, Methyl benzoate | " | " | 1.24 | 1.27 |
| Salicylic acid, Methyl salicylate | " | " | 1.27 | 1.21 |
| Salicylic acid, Cinnamic acid, Methyl salicylate | $(1/3)^3$ | $(2/5)^3$ | 1.23 | 1.25 |
| Salicylic acid, Methyl benzoate, Trimellitic anhyd. | " | " | 1.23 | 1.21 |

TABLE 5

Extractive Agents Which Contain Aromatic Anhydrides

| Compounds | Ratios | | Relative Volatilities | |
|---|---|---|---|---|
| Phthalic anhydride, Methyl benzoate | $(1/2)^2$ | $(3/5)^2$ | 1.18 | 1.18 |
| Phthalic anhydride, Methyl salicylate | " | " | 1.19 | 1.21 |
| Hexahydrophthalic anhydride (HHphanh) | 1 | 6/5 | 1.17 | 1.16 |
| HH ph anh., Benzyl benzoate | $(1/2)^2$ | $(3/5)^2$ | 1.13 | 1.24 |
| HH ph anh., Methyl benzoate | " | " | 1.22 | 1.21 |
| HH ph anh., Methyl salicylate | " | " | 1.23 | 1.22 |
| HH ph anh., Benzoic acid | " | " | 1.20 | 1.20 |
| HH ph anh., Salicylic acid | " | " | 1.18 | 1.20 |
| HH ph anh, Benzoic acid, Methyl benzoate | $(1/3)^3$ | $(2/5)^3$ | 1.21 | 1.19 |
| HH ph anh, Benzoic acid, Methyl salicylate | " | " | 1.24 | 1.21 |
| HH ph anh, Benzoic acid, Butyl benzyl phthalate | " | " | 1.17 | 1.15 |
| HH ph anh, Salicylic acid, Methyl benzoate, | " | " | 1.20 | 1.21 |
| HH ph anh, Phthalic anhydride, Benzyl benzoate | " | " | 1.13 | 1.18 |
| HH ph anh, Phthalic anhydride, Methyl benzoate | " | " | 1.16 | 1.19 |
| HH ph anh, Phthalic anhydride, Methyl salicylate | " | " | 1.18 | 1.13 |
| HH ph anh, Methyl benzoate, Trimellitic anhydride | " | " | 1.18 | 1.11 |
| Methyl hexahydro phthalic anhydride (MeHH ph anh) | 1 | | 1.19 | — |
| MeHH ph anh, Benzyl benzoate | $(1/2)^2$ | $(3/5)^2$ | 1.19 | 1.20 |
| MeHH ph anh, Methyl salicylate | " | " | 1.24 | 1.10 |
| MeHH ph anh, Benzoic acid | " | " | 1.20 | 1.20 |
| MeHH ph anh, Cinnamic acid | " | " | 1.18 | 1.20 |
| MeHH ph anh, Salicylic acid | " | " | 1.20 | 1.17 |
| MeHH ph anh, HH ph anh. | " | " | 1.16 | 1.21 |
| MeHH ph anh, Phthalic anhydride | " | " | 1.09 | 1.11 |
| MeHH ph anh, Benzoic acid, Benzyl benzoate | $(1/3)^3$ | $(2/5)^3$ | 1.16 | 1.16 |
| MeHH ph anh, Benzoic acid, Methyl benzoate | " | " | 1.22 | 1.20 |
| MeHH ph anh, Benzoic acid, Cinnamic acid | " | " | 1.22 | 1.19 |
| MeHH ph anh, Phthalic anhydride, HH ph anh. | " | " | 1.14 | — |
| MeHH ph anh, Phthalic anhydride, Methyl salicylate | " | " | 1.21 | 1.17 |

TABLE 5-continued

| Extractive Agents Which Contain Aromatic Anhydrides | | | | |
|---|---|---|---|---|
| Compounds | Ratios | | Relative Volatilities | |
| MeHH ph anh, Salicylic acid, Methyl salicylate | " | " | 1.22 | 1.20 |
| MeHH ph anh, Salicylic acid, Methyl benzoate | " | " | 1.20 | 1.19 |
| MeHH ph anh, Methyl benzoate, Benzoic acid, Cinnamic acid | $(1/4)^4$ | $(1/3)^4$ | 1.17 | 1.24 |
| MeHH ph anh, Methyl benzoate, Phthalic anhydride, Salicylic acid | " | " | 1.17 | 1.22 |
| Trimellitic anhydride, Methyl benzoate | $(1/2)^2$ | $(3/5)^2$ | 1.22 | 1.25 |

TABLE 6

| Miscellaneous Extractive Agents Which Are Effective | | | | |
|---|---|---|---|---|
| Compounds | Ratios | | Relative Volatilities | |
| Methyl benzoate | 1 | 6/5 | 1.20 | 1.24 |
| Methyl salicylate | " | " | 1.17 | 1.13 |

One third parts of benzoic acid plus ⅓ parts of phthalic anhydride plus ⅓ parts of methyl benzoate mixed with one part of n-propanol-2-butanol mixture gives a relative volatility of 1.19, with 2/5 parts, these three give 1.20. In every example in Table 2, 3, 4, 5 and 6 the starting material is a 50—50% mixture of n-propanol-2-butanol which possesses a relative volatility of 1.07.

Several of the compounds listed in Tables 2, 3, 4, 5 and 6 and whose relative volatility had been determined in the vapor-liquid equilibrium still, were then evaluated in a glass perforated plate rectification column possessing 4.5 theoretical plates. The results are listed in Table 7. The n-propanol-2-butanol mixture used conatined 50% n-propanol. The first run is with no extractive agent and with 400 grams of about 50% mixture in the stillpot. After 60 minutes of operation, the separation is that in accordance with a relative volatility of 1.06. Further operation for another hour does not change the relative volatility. The second run is with methyl salicylate as the extractive agent and here a relative volatility of 1.21 is obtained. This compares with the 1.17 and 1.12 shown for methyl salicylate in Table 6., the data for which was obtained in the vapor-liquid equilibrium still. The third run is with a mixture comprising 83% methyl salicylate, 17% cinnamic acid. This agent gives a relative volatility of 1.23 which may be compared with values of 1.27 and 1.21 in Table 3. The fourth run is with methyl benzoate which gave an average relative volatility of 1.23. In Table 6, this agent gave relative volatilities of 1.20 and 1.24. The fifth run is with methyl benzoate and cinnamic acid which gave an average relative volatility of 1.18 and can be compared with 1.19 and 1.20 shown in Table 3. The sixth run is with methyl benzoate and salicylic acid which gave an average relative volatility of 1.18 and can be compared with 1.24 and 1.27 shown in Table 4.

THE USEFULNESS OF THE INVENTION

The usefulness or utility of this invention can be demonstrated by referring to the data presented in Tables 2, 3, 4, 5, 6 and 7. All of the successful extractive distillation agents show that n-propanol can be removed from 2-butanol by means of distillation in a rectification column and that the ease of separation as measured by relative volatility is considerable. Without these extractive distillation agents, virtually no improvement will occur in the rectification column. The data also show that the most attractive agents will operate at a boilup rate low enough to make this a useful and efficient method of recovering high purity n-propanol from any mixture with 2-butanol. The stability of the compounds used and the boiling point difference is such that complete recovery and recycle is obtainable by a simple distillation and the amount required for make-up is small.

TABLE 7

| | Data From Runs Made In Rectification Column. | | | | | | |
|---|---|---|---|---|---|---|---|
| Agent | Time min. | Stillpot at Start | Temp. °C. Sampling | Overhead Temp. when Sampling | Weight % Overhead | n-Propanol Bottoms | Relative Volatility |
| None | 60 | 96.6 | 97.2 | 84.6 | 49.0 | 42.6 | 1.06 |
| " | 90 | 96.6 | 96.8 | 87.8 | 49.1 | 41.9 | 1.07 |
| " | 120 | 96.6 | 96.6 | 89.2 | 49.4 | 41.8 | 1.07 |
| | | | | | | Average = | 1.07 |
| Methyl salicylate | 60 | 100.8 | 113.2 | 83.2 | 61.7 | 41.8 | 1.20 |
| Methyl salicylate | 80 | 100.8 | 117.6 | 83.4 | 63.9 | 42.2 | 1.22 |
| Methyl salicylate | 100 | 100.8 | 121.2 | 88.6 | 61.7 | 41.5 | 1.22 |
| | | | | | | Average = | 1.21 |
| Methyl salicylate, Cinnamic acid | 60 | 98.0 | 121.2 | 83.4 | 65.2 | 42.4 | 1.23 |
| Methyl salicylate, Cinnamic acid | 90 | 98.0 | 131.6 | 87.6 | 62.8 | 42.0 | 1.21 |
| Methyl salicylate, Cinnamic acid | 120 | 98.0 | 136.2 | 89.6 | 64.6 | 41.2 | 1.24 |
| | | | | | | Average = | 1.23 |
| Methyl benzoate | 60 | 100.2 | 112.8 | 82.6 | 63.9 | 42.8 | 1.21 |
| Methyl benzoate | 90 | 100.8 | 122.8 | 92.0 | 65.6 | 41.7 | 1.24 |

TABLE 7-continued

| | | | | | | | |
|---|---|---|---|---|---|---|---|
| Methyl benzoate | 120 | 100.8 | 128.4 | 91.8 | 64.7 | 41.7 | 1.23 |
| | | | | | | Average = | 1.23 |
| Methyl benzoate, Cinnamic acid | 60 | 99.4 | 119.4 | 84.4 | 60.5 | 43.5 | 1.17 |
| Methyl benzoate, Cinnamic acid | 90 | 99.4 | 128.2 | 85.8 | 61.9 | 43.4 | 1.18 |
| Methyl benzoate, Cinnamic acid | 120 | 99.4 | 135.0 | 84.6 | 62.4 | 42.2 | 1.20 |
| | | | | | | Average = | 1.18 |
| Methyl benzoate, Salicylic acid | 60 | 96.6 | 129.2 | 82.4 | 59.4 | 41.3 | 1.18 |
| Methyl benzoate, Salicylic acid | 90 | 96.6 | 136.0 | 79.4 | 59.2 | 38.3 | 1.17 |
| Methyl benzoate, Salicylic acid | 120 | 96.6 | 144.2 | 78.4 | 59.9 | 40.5 | 1.19 |
| | | | | | | Average = | 1.18 |

| Notes Agent | Feed, Wt. % n-PrOH | Agent Flow Rate, ml/min | Boilup Rate ml/min | Agent Temp. °C. | Agent Comp. Wt % |
|---|---|---|---|---|---|
| None | 50 | 20 | 10-20 | — | — |
| Methyl salicylate | 50 | 20 | 10-20 | 80-85 | 100 |
| Methyl salicylate, Cinnamic acid | 50 | 20 | 10-20 | 75-85 | 83 MeSal. |
| Methyl benzoate | 50 | 20 | 10-20 | 85-95 | 100 |
| Methyl salicylate, Cinnamic acid | 50 | 20 | 10-20 | 70-80 | 83 MeBen. |
| Methyl benzoate, Salicylic acid | 50 | 20 | 10-20 | 80-85 | 80 MeBen. |

WORKING EXAMPLES

Example 1

Twenty-five grams of n-propanol, 25 grams of 2-butanol and fifty grams of methyl benzoate were charged to an Othmer type glass vapor-liquid equilibrium still and refluxed for 16 hours. Analysis of the vapor and liquid by gas chromatography gave a vapor composition of 46% n-propanol, 54% 2-butanol; a liquid composition of 41.6% n-propanol, 58.4% 2-butanol. This indicates a relative volatility of 1.20. Ten grams of methyl benzoate were added and refluxing continued for another ten hours. Analysis indicated a vapor composition of 46% n-propanol, 54% 2-butanol; a liquid composition of 40.8% n-propanol, 59.2% 2-butanol which is a relative volatility of 1.24.

Example 2

Fifty grams of the n-propanol-2-butanol mixture, 25 grams of benzoic acid and 25 grams of methyl benzoate were charged to the vapor-liquid equilibrium still and refluxed for 13 hours. Analysis indicated a vapor composition of 46% n-propanol, 54% 2-butanol, a liquid composition of 40.9% n-propanol, 59.1% 2-butanol which is a relative volatility of 1.23. Five grams of benzoic acid and five grams of methyl benzoate were added and refluxing continued for another eleven hours. Analysis indicated a vapor composition of 45.6% n-propanol, 54.4% 2-butanol; a liquid composition of 40.3% n-propanol, 59.7% 2-butanol which is a relative volatility of 1.24.

Example 3

Fifty grams of the n-propanol-2-butanol mixture, 17 grams of cinnamic acid, 17 grams of phthalic anhydride and 17 grams of methyl benzoate were charged to the vapor-liquid equilibrium still and refluxed for twelve hours. Analysis indicated a vapor composition of 41.7% n-propanol, 58.3% 2-butanol; a liquid composition of 36.5% n-propanol, 63.5% 2-butanol which is a relative volatility of 1.24. Three grams each of cinnamic acid, phthalic anhydride and methyl benzoate were added and refluxing continued for another twelve hours. Analysis indicated a vapor composition of 40.6% n-propanol, 59.4% 2-butanol and a liquid composition of 34.8% n-propanol, 65.2% 2-butanol which is a relative volatility of 1.28.

Example 4

A glass perforated plate rectification column was calibrated with ethylbenzene and p-xylene which possesses a relative volatility of 1.06 and found to have 4.5 theoretical plates. A solution of 200 grams of n-propanol and 200 grams of 2-butanol was placed in the stillpot and heated. When refluxing began, an extractive agent consisting of pure methyl benzoate was pumped into the column at a rate of 20 ml/min. The temperature of the extractive agent as it entered the column was 70°-80° C. After establishing the feed rate of the extractive agent, the heat input to the n-propanol-2-butanol in the stillpot was adjusted to give a reflux rate of 10-20 ml/min. After one hour of operation, overhead and bottoms samples of approximately two ml. were collected and analysed using gas chromatography. The overhead analysis was 63.9% n-propanol, 36.1% 2-butanol. The bottoms analysis was 42.8% n-propanol, 57.2% 2-butanol. Using these compositions in the Fenske equation, with the number of theoretical plates in the column being 4.5, gave an average relative volatility of 1.21 for each theoretical plate. After 1.5 hours of total operating time, the overhead and bottoms samples were again taken and analysed. The overhead composition was 65.6% n-propanol, 34.4% 2-butanol and the bottoms composition was 41.7% n-propanol, 58.3% 2-butanol. This gave an average relative volatility of 1.24 for each theoretical plate. After two hours of total operating time, the overhead and bottoms samples were again taken and analysed. The overhead composition was 64.7% n-propanol, 35.3% 2-butanol and the bottoms composition was 41.7% n-propanol, 58.3% 2-butanol. This gave an average relative volatility of 1.23 for each theoretical plate.

Example 5

A solution of 200 grams of n-propanol and 200 grams of 2-butanol was placed in the stillpot of the same column used in example 4 and heat applied. When refluxing began, an extractive agent comprising 83% methyl salicylate, 17% cinnamic acid was fed to the top of the column at a feed rate of 20 ml/min. and a temperature of 75°–80° C. After establishing the feed rate of the extractive agent, the heat input to the n-propanol-2-butanol in the stillpot was adjusted to give a total reflux rate of 10–20 ml/min. Having established the reflux rate, the column was allowed to operate for one hour. After one hour of steady operation, overhead and bottoms samples of approximately two ml. were collected and analysed by gas chromatography. The overhead analysis was 65.2% n-propanol, 34.8% 2-butanol; the bottoms analysis was 42.4% n-propanol, 57.6% 2-butanol. Using these compositions in the Fenske equation with the number of theoretical plates in the column being 4.5, gave an average relative volatility of 1.23 for each theoretical plate. After 1.5 hours of total operation, the overhead composition was 62.8% n-propanol, 37.2% 2-butanol and the bottoms composition was 42% n-propanol, 58% 2-butanol. This gave an average relative volatility of 1.21 for each theoretical plate. After two hours of total operation, the overhead composition was 64.6% n-propanol, 35.4% 2-butanol and the bottoms composition was 41.2% n-propanol, 58.8% 2-butanol. This gave an average relative volatility of 1.24 for each theoretical plate.

What is claimed is:

1. A method for recovering n-propanol from a mixture of n-propanol and 2-butanol which comprises distilling a mixture of n-propanol and 2-butanol in a rectification column in the presence of about one to two parts of extractive agent per part of n-propanol-2-butanol mixture, recovering n-propanol as overhead product, obtaining the 2-butanol and the extractive agent from the stillpot, separating the 2-butanol from the extractive agent by conventional distillation in another rectification column, wherein said extractive agent
   (1) is an organic compound or a mixture of organic compounds composed solely of carbon, hydrogen and oxygen and contain a six carbon atom aromatic ring
   (2) boils at least 100 Centigrade degrees above n-propanol
   (3) does not form binary azeotropes with either n-propanol or 2-butanol
   (4) does not form a ternary azeotrope with n-propanol and 2-butanol
   (5) is miscible in boiling n-propanol-2-butanol mixtures
   (6) in combination with n-propanol and 2-butanol, results in a relative volatility of n-propanol to 2-butanol in the range of 1.09 to 1.27.

2. The process of claim 1 wherein the extractive agent is selected from a member of the group consisting of methyl benzoate, methyl salicylate, hexahydrophthalic anhydride and methyl hexahydro-phthalic anhydride.

3. The process of claim 1 wherein the extractive agent is selected from mixtures consisting of at least two compounds from the group consisting of methyl benzoate, methyl salicylate, hexahydro-phthalic anhydride, methyl hexahydrophthalic anhydride, benzoic acid, benzyl benzoate, phthalic anhydride, methyl tetrahydro-phthalic anhydride, salicylic acid, cinnamic acid, trimellitic anhydride and butyl benzyl phthalate.

* * * * *